(12) United States Patent
Li et al.

(10) Patent No.: US 10,793,536 B2
(45) Date of Patent: Oct. 6, 2020

(54) VORTIOXETINE PAMOIC ACID SALT AND CRYSTAL FORM THEREOF

(71) Applicant: SHANGHAI SYNERGY PHARMACEUTICAL SCIENCES CO., LTD, Shanghai (CN)

(72) Inventors: Yunfei Li, Shanghai (CN); Xiaoer Xia, Shanghai (CN); Xin Xu, Shanghai (CN); Zhen Zhang, Shanghai (CN); Lei Liu, Shanghai (CN); Xiaojuan Zhang, Shanghai (CN); Liming Zhang, Shanghai (CN); Dongsheng Li, Shanghai (CN); Yijin Wang, Shanghai (CN); Jian Ge, Shanghai (CN)

(73) Assignee: SHANGHAI SYNERGY PHARMACEUTICAL SCIENCES CO., LTD, Shanghai (CN)

( * ) Notice: Subject to any disclaimer, the term of this patent is extended or adjusted under 35 U.S.C. 154(b) by 0 days.

(21) Appl. No.: 16/086,615

(22) PCT Filed: Mar. 28, 2017

(86) PCT No.: PCT/CN2017/078427
§ 371 (c)(1),
(2) Date: Sep. 20, 2018

(87) PCT Pub. No.: WO2017/167180
PCT Pub. Date: Oct. 5, 2017

(65) Prior Publication Data
US 2019/0169147 A1    Jun. 6, 2019

(30) Foreign Application Priority Data
Mar. 29, 2016 (CN) .......................... 2016 1 0187639

(51) Int. Cl.
*C07D 295/096* (2006.01)
*A61K 31/495* (2006.01)
*C07C 65/11* (2006.01)
*C07C 51/41* (2006.01)

(52) U.S. Cl.
CPC ........ *C07D 295/096* (2013.01); *A61K 31/495* (2013.01); *C07C 51/41* (2013.01); *C07C 65/11* (2013.01); *C07B 2200/13* (2013.01)

(58) Field of Classification Search
CPC ..... C07D 295/096; C07C 51/41; C07C 65/11; C07B 2200/13; A61K 31/495
USPC .................................................. 514/255.03
See application file for complete search history.

(56) References Cited

FOREIGN PATENT DOCUMENTS

| CN | 1136779 A | 11/1996 |
|---|---|---|
| CN | 102614179 A | 8/2012 |
| CN | 104039765 A | 9/2014 |
| WO | 2007144005 A1 | 12/2007 |
| WO | 2015114395 A1 | 8/2015 |

OTHER PUBLICATIONS

International Search Report for PCT application No. PCT/CN2017/078427 filed on Mar. 28, 2017, dated Jun. 27, 2017.
JP Lindenmayer:"Neuropsychiatric Disease and Treatment Long-acting injectable antipsychotics: focus on olanzapine pamoate", Neuropsychiatric Disease and Treatment, Jan. 1, 2010 (Jan. 1, 2010), pp. 6-261, XP055321200, Retrieved from the Internet: URL: https://www.ncbi.nlm.nih.gov/pmc/articles/PMC2898165/pdf/ndt-6-261.pdf.
European Search Report for corresponding application 17773210.4; Report dated Dec. 19, 2018.

*Primary Examiner* — Kristin A Vajda
(74) *Attorney, Agent, or Firm* — Gang Yu (57) ABSTRACT

The present application provides a vortioxetine pamoic acid salt, which includes a crystal form, a solvate or an amorphous substance of the vortioxetine pamoic acid salt. The present application provides a preparation method and use of the vortioxetine pamoic acid salt and the crystal form thereof. The vortioxetine pamoic acid salt prepared in the present application prolongs the residence time of the vortioxetine in vivo, achieving a slow release of the vortioxetine in vivo, and is suitable for preparing a long-acting dosage form.

20 Claims, 5 Drawing Sheets

VORTIOXETINE PAMOIC ACID SALT AND CRYSTAL FORM THEREOF

TECHNICAL FIELD

The present application relates to the field of medicine research and development, in particular to the vortioxetine pamoic acid salt and the crystal form thereof, and the preparation method and use thereof.

BACKGROUND

Vortioxetine, with the chemical name 1-[2-(2,4-dimethyl phenylthioruea alkyl) phenyl] piperazine, is an antidepressant jointly developed by Takeda Pharma and Lundbeck. This drug appeared on the market in the name of Brintellix after approval by the U.S. FDA in September 2013. On the one hand, this drug acts as an inhibitor of 5-HT transport protein (SERT), playing the role of preventing emotional disorders such as depression or anxiety by inhibiting the reuptake of 5-serotonin; on the other hand, vortioxetine also has the functions of $5-HT_{1A}$ receptor agonist, $5-HT_{1B}$ receptor partial agonist and $5-HT_3$, $5-HT_{1D}$ and $5-HT_7$ receptor antagonists. The pharmacological mechanism suggests that vortioxetine can also be used to treat pain and depression related disorders, such as cognitive impairment or sleep disorders in patients with depression. As the first antidepressant with multiple pharmacodynamic activities, vortioxetine is expected to become a successful new drug in the market of depression.

Free vortioxetine has a low biological availability in vivo. In order to increase the biological availability of vortioxetine in vivo, researchers prepare various salts and crystal forms of vortioxetine. Patents WO2007144005 and WO014044721 disclose various medicinal salts of vortioxetine, involving preparation methods of vortioxetine hydrobromide and 5 crystal forms thereof; WO2010121621 discloses the preparation method of vortioxetine lactate; CN104628677 discloses crystal forms of vortioxetine for hydroxy benzoate and its hydrate; CN104610195 discloses crystal forms of vortioxetine for aspartate and its hydrate. Compared with free vortioxetine compounds, the vortioxetine salts are improved in some degrees in terms of solubility, stability and bioavailability.

However, there isn't any technical report yet that pharmaceutically acceptable salts of vortioxetine can retard the release rate of vortioxetine in vivo and prolong the duration of vortioxetine exerting its medical effect in vivo.

SUMMARY

The objective of the present application is to provide a vortioxetine pamoic acid salt and a crystal form thereof. For the first time vortioxetine and pamoic acid are used in a certain ratio to prepare a salt, which prolongs the residence time of vortioxetine in vivo and achieves a slow release of vortioxetine in vivo. Vortioxetine pamoic acid salt can be prepared into a stable long-acting drug, which can be administered to the patient once every two weeks or once every four weeks, this may greatly improve the drug using efficiency, improve the therapeutic effect of the drug, improve the patient's compliance and reduce adverse reactions.

The present application provides vortioxetine pamoic acid salt, and the structure of this substance can be expressed by the formula $(C_{18}H_{22}N_2S)_r \cdot C_{23}H_{16}O_6 \cdot nH_2O$, wherein r is 1 or 2, preferably 2, n=0~10, preferably an integer from 0 to 6, the vortioxetine pamoic acid salt includes crystalline substance, solvate or amorphous substance, wherein when n=0, the crystalline substance is an anhydrous crystal form; when n is not 0, the crystalline substance is hydrate crystal, and the crystalline substance can also be polymorphic.

The solid form of the salt or polycrystalline form of the present application can have a variety of different internal structures and physical and chemical properties, which depends on the reaction conditions for synthesizing the salts or eutectics or the conditions of crystallization/cocrystallization. In addition, the solid form of the salt or polycrystalline form of the present application can be a crystal of the eutectic of the salt or a mixture of amorphous forms. However, preferably the solid form of a single crystal or eutectic of the salt in the present application does not include an amorphous structure.

The vortioxetine pamoic acid salt in the present application is of crystal form A, and in the X ray powder diffraction pattern of this crystal form, there are peaks at the positions where 2θ is 12.96±0.2, 13.56±0.2, 16.67±0.2, 17.26±0.2 and 18.28±0.2 degrees.

Further, crystal form A also has peaks at one or more of the positions where 2θ is 14.77±0.2, 18.28±0.2, 18.77±0.2, 19.98±0.2, 22.08±0.2, 23.03±0.2 degrees, or in the X ray powder diffraction pattern of this crystal form, there are peaks at one or more of the positions where 2θ is 11.71±0.2, 12.41±0.2, 12.96±0.2, 13.56±0.2, 14.77±0.2, 16.67±0.2, 17.26±0.2, 18.28±0.2, 18.77±0.2, 19.98±0.2, 21.02±0.2, 22.08±0.2, 23.03±0.2, 24.03±0.2, 24.99±0.2, 25.94±0.2, 27.33±0.2, 27.99±0.2, 29.80±0.2, 30.59±0.2, 31.09±0.2, 32.70±0.2, 35.46±0.2, 39.21±0.2, 42.81±0.2, and 46.98±0.2 degrees.

The vortioxetine pamoic acid salt in the present application is of crystal form B, and in the X ray powder diffraction pattern of this crystal form, there are peaks at the positions where 2θ is 15.23±0.2, 19.37±0.2, and 22.24±0.2 degrees.

Further, crystal form B also has peaks at one or more of the positions where 2θ is 12.50±0.2, 14.93±0.2, 23.25±0.2, 24.49±0.2, 28.28±0.2, 30.58±0.2 degrees, or in the X ray powder diffraction pattern of this crystal form, there are peaks at one or more of the positions where 2θ is 11.89±0.2, 12.50±0.2, 14.93±0.2, 15.23±0.2, 18.63±0.2, 19.37±0.2, 20.15±0.2, 22.24±0.2, 23.25±0.2, 24.49±0.2, 24.82±0.2, 28.28±0.2, 30.58±0.2, 36.97±0.2, 37.58±0.2, 38.73±0.2, 40.67±0.2, and 41.81±0.2 degrees.

The vortioxetine pamoic acid salt in the present application is of crystal form D, and in the X ray powder diffraction pattern of this crystal form, there are peaks at the positions where 2θ is 12.34±0.2, 16.16±0.2, and 18.05±0.2 degrees.

Further, crystal form D also has peaks at one or more of the positions where 2θ is 11.51±0.2, 16.48±0.2, 17.69±0.2, 19.36±0.2, 21.50±0.2, 22.50±0.2, 24.01±0.2, 27.65±0.2 degrees, or in the X ray powder diffraction pattern of this crystal form, there are peaks at one or more of the positions where 2θ is 11.51±0.2, 12.34±0.2, 13.66±0.2, 14.56±0.2, 16.16±0.2, 16.48±0.2, 17.69±0.2, 18.05±0.2, 18.83±0.2, 19.36±0.2, 20.09±0.2, 21.20±0.2, 21.50±0.2, 22.50±0.2, 24.01±0.2, 24.96±0.2, 26.40±0.2, 26.94±0.2, 27.62±0.2, 28.46±0.2, 29.59±0.2, 30.58±0.2, 31.08±0.2, 31.28±0.2, 35.81±0.2, 41.45±0.2, 41.51±0.2, 43.38±0.2, and 48.23±0.2 degrees.

The crystal form in the present application is basically pure, wherein "basically pure" means that purity of the crystal form is at least 60%, or at least 70%, or at least 80%, or at least 85%, or at least 90%, or at least 93%, or at least 95%, or at least 98%, or at least 99%.

The preparation method of the vortioxetine pamoic acid salt disclosed in the present application is as follows: tripping an aqueous solution (or turbid solution) of acid of vortioxetine to an aqueous alkaline solution of pamoic acid at a room temperature for a neutralization reaction to generate a vortioxetine pamoic acid salt, wherein the acid may be hydrochloric acid, sulfuric acid, phosphoric acid, hydrobromic acid, and acetic acid, and preferably acetic acid, wherein the alkali may be ammonia water, potassium carbonate, sodium carbonate, triethylamine, pyridine, and sodium hydroxide, and preferably sodium hydroxide.

The preparation method of crystal form A of the vortioxetine pamoic acid salt disclosed in the present application is as follows: adding vortioxetine and pamoic acid with a mole ratio of 2:1 to an organic solvent, wherein the ratio of weight (g) of vortioxetine to volume (ml) of the organic solvent during the reaction is 1: (5~40), heating to a temperature of 30~80 C, preferably 50~60 C, stirring for dissolution for 1-2 hours, then leaving it undisturbed or stirring for crystallization for 1~48 hours, (or rapidly cooling the supernatant after leaving it undisturbed, or naturally cooling the supernatant after leaving it undisturbed, or naturally volatilizing the supernatant after leaving it undisturbed), separating out crystals, performing suction filtration, performing vacuum drying under 40~50° C. to obtain finished products, wherein the organic solvents may be alcohols, such as methanol, ethanol, n-propanol, isopropanol, n-butanol, 2-butanol, 2-methyl-1-propanol, and 2-methyl-2-propanol or tertiary butanol; ester solvents such as ethyl acetate, n-propyl acetate, isopropyl acetate, n butyl acetate, isobutyl acetate, sec-butyl acetate, tertiary butyl acetate; ether solvents, such as diethyl ether, dibutyl ether, butyl methyl ether, secondary butyl methyl ether, tetrahydrofuran, dioxy heterocyclic ethane, dimethoxy ethane, diglycol dimethyl ether, methyl tetrahydrofuran, dioxane, ethylene glycol dimethyl ether, methyl tert butyl ether, or isopropyl ether; ketone solvents, such as acetone, methyl ethyl ketone, methyl isobutyl ketone, cyclohexanone, or 4-methyl-2-pentanone; alkane solvents, such as dichloromethane, 1,2-dichloroethane, chloroform, carbon tetrachloride, nitroethane, hexane, n-hexane, cyclohexane, pentane or n-heptane; aromatic solvents, such as benzene, toluene, or xylene; nitrile solvents, such as acetonitrile or malononitrile; amide solvents, such as formamide, dimethyl formamide, dimethyl acetamide, N-methyl-2-pyrrolidone and hexamethyl phosphor triacid amide. The organic solvent is preferably one of ethanol, acetonitrile, acetone, ethyl acetate, dimethyl sulfoxide and tetrahydrofuran or a mixed solvent of at least two of ethanol, acetonitrile, acetone, ethyl acetate, dimethyl sulfoxide and tetrahydrofuran.

The preparation method of crystal form B of the vortioxetine pamoic acid salt disclosed in the present application is as follows: adding vortioxetine and pamoic acid with a mole ratio of 2:1 to an organic solvent, and adding insoluble solvent swelling crystals, wherein the ratio of weight (g) of vortioxetine to volume (ml) of the organic solvent during the reaction is 1: (3~10), and the volume (ml) ratio of the organic solvent to the insoluble solvent is 1: (1~20), separating out crystals and performing suction filtration, carrying out vacuum drying at 40~50° C. to obtain finished products, wherein the organic solvent may be solvents such as DMSO and THF, and the insoluble solvent is aqueous solution of methanol, aqueous solution of ethanol or aqueous solution of acetone.

The preparation method of crystal form D of the vortioxetine pamoic acid salt disclosed in the present application is as follows: adding vortioxetine and pamoic acid with a mole ratio of 2:1 to an organic solvent, wherein the ratio of weight (g) of vortioxetine to volume (ml) of the organic solvent during the reaction is 1: (5~40), stirring at room temperature for 3-6 days, separating out crystals and performing suction filtration, carrying out vacuum drying at 40~50° C. to obtain finished products, wherein the organic solvent may be solvents such as acetonitrile and acetone.

The preparation method of the vortioxetine pamoic acid salt monohydrate disclosed in the present application is as follows: dissolving vortioxetine into a mixed solvent of organic solvent and water, heating for reflux dissolution, wherein the dissolution temperature is 30~80° C. or 40~60° C., and adding pamoic acid, wherein the mole ratio of pamoic acid to vortioxetine is 1:2 or 1:1, stirring for dissolution, leaving it undisturbed at room temperature or stirring for separation of crystals (1-72 hours later, crystals are separated out), performing suction filtration, carrying out vacuum drying at 40~50° C. to obtain finished products, wherein the organic solvent is preferably one of ethanol, acetonitrile, acetone, ethyl acetate, dimethyl sulfoxide and tetrahydrofuran, or a mixed solvent of at least two of ethanol, acetonitrile, acetone, ethyl acetate, dimethyl sulfoxide and tetrahydrofuran.

The present application further provides a pharmaceutical composition containing the crystalline or amorphous form of the above vortioxetine pamoic acid salt as an active ingredient, as well as pharmaceutically acceptable excipients and/or carriers, the pharmaceutical composition can be further prepared into an injection, wherein the active ingredient exerts the medical effect in the human body for at least 24 hours, 48 hours, 72 hours, 96 hours, 120 hours, 144 hours, 168 hours, 192 hours, 216 hours, 240 hours, 264 hours, 288 hours, 312 hours, 336 hours, 360 hours, 384 hours, 408 hours, 432 hours, 456 hours, 480 hours, 504 hours, 528 hours, 552 hours, 576 hours, 600 hours, 624 hours, 648 hours, 672 hours, 696 hours, and 720 hours.

The single dose of the pharmaceutical composition in the present application varies with the weight of the patient, the method of administration, and the severity of the disease or pain. The single dose of the salt or the crystal thereof in the present application is 5-1500 mg or 10-1000 mg, preferably 10 mg, 20 mg, 30 mg, 40 mg, 50 mg, 60 mg, 70 mg, 80 mg, 100 mg, 120 mg, 140 mg, 150 mg, 160 mg, 180 mg, 200 mg, 220 mg, 240 mg, 260 mg, 280 mg, 300 mg, 320 mg, 340 mg, 350 mg, 360 mg, 380 mg, 400 mg, 420 mg, 450 mg, 460 mg, 480 mg, 500 mg, 520 mg, 540 mg, 550 mg, 570 mg, 580 mg, 600 mg, 620 mg, 640 mg, 650 mg, 680 mg, 700 mg, 720 mg, 740 mg, 750 mg, 780 mg, 800 mg, 820 mg, 840 mg, 850 mg, 860 mg, 880 mg, 900 mg, 920 mg, 940 mg, 950 mg or 980 mg.

The composition provided in the present application can be administered outside the gastrointestinal tract, and the active compound can be dissolved in a pharmaceutical carrier to be prepared as a suspension. The pharmaceutical carrier is preferably a viscous injectable carrier. For example, the carrier is at least 20 cp when its viscosity is 20 C°; when the viscosity of the liquid phase of the suspension is 20 C, the suspension is at least about 30 cp, 40 cp, 50 cp or 60 cp. The pharmaceutical carrier may also include viscosity reinforcers, density reinforcers, tension reinforcers and/or wetting agents. Suitable pharmaceutical carriers include water, brine, dextrose solution, fructose solution, ethanol or animal, plant or oil from a synthetic source. The pharmaceutical carrier can also contain preservatives and buffering agents.

The composition provided in the present application may be prepared into a reagent administered through percutaneous administration, intramuscular injection and intravenous injection; in addition to the active ingredient vortioxetine pamoic acid salt, the reagent further comprises wetting agents, e.g. polyoxyethylene derivatives of dehydrated sorbitol, such as polysorbate 80 (Tween-80) and polysorbate 20 (Tween-20), lecithin, polyoxyethylene ether, polyoxypropylene ether, sodium deoxycholate, poloxamer, and mannitol; suspending agents, e.g. cellulose derivatives, such as methyl cellulose, sodium carboxymethyl cellulose and hydroxypropyl methyl cellulose, polyvinyl pyrrolidone, alginate, chitosan, dextran, gelatin, polyethylene glycol, polyoxyethylene ether and polyoxypropylene ether; buffer solution, a mixture containing an appropriate amount of acid (such as phosphoric acid, succinic acid, tartaric acid, lactic acid, acetic acid, maleic acid or citric acid) and an appropriate amount of alkali (especially sodium hydroxide or disodium hydrogen phosphate). On the other hand, vortioxetine pamoic acid salt can also be prepared in one or more oils, such as peanut oil, sesame oil, cottonseed oil, corn oil, safflower oil, castor oil, ethyl oleate, soybean oil, synthetic glyceride of long chain fatty acids or medium chain acids, as well as mixtures of these oils and other oils. In addition, thickeners such as aluminum monostearate, ethyl cellulose, triglycerides, and hydrogenated castor oil can also be added to the composition preparation.

The crystal form, amorphous form or pharmaceutical composition provided in the present application can be used on pharmaceuticals for prevention and treatment of nervous system diseases, including depression, postpartum depression, treatment-resistant depression, depression related to bipolar disorder, anxiety, obsessive-compulsive disorder, panic disorder, drug abuse, alcoholism, nicotine addiction, carbohydrate addiction, Alzheimer's disease, cognitive impairment, chronic pain, neuropathic pain, nociceptive pain, inflammatory pain, visceral pain, migraine, and cancer related pain.

Beneficial Effects

1. The vortioxetine pamoic acid salt in the present application prolongs the residence time of vortioxetine in vivo, reduces the release speed of vortioxetine in vivo, achieves a slow release of vortioxetine in vivo, and prolongs the duration of medical effect of vortioxetine in vivo.

2. Vortioxetine pamoic acid salt in the present application can be prepared into a stable long-acting drug, which can be administered to the patient once every two weeks or once every four weeks, this may greatly improve the drug using efficiency, improve the therapeutic effect of the drug, improve the patient's compliance and reduce adverse reactions.

DETAILED DESCRIPTION OF THE EMBODIMENTS

The present application will be described below with reference to the embodiments.

Example 1: Preparation of Vortioxetine Pamoic Acid Salt (r=1)

Dissolving vortioxetine (84.3 g, 283 mmol) and glacial acetic acid (17 g, 283 mmol) in 900 milliliter water at room temperature, adding pamoic acid (109.9 g, 283 mmol) and sodium hydroxide (11.3 g, 283 mmol) to the 900 milliliter water respectively, stirring for dissolution, dripping the above prepared vortioxetine acetic acid solution to NaOH aqueous solution of pamoic acid for neutral reaction, stirring for two hours, filtering, washing the filter cake with water for three times, and drying using 50° C. air to obtain a yellow solid, and verifying the product using nuclear magnetic resonance hydrogen spectrum and mass spectrum. $^1$H NMR (400 MHz, DMSO) δ: 8.90 (s, 2H), 8.37 (s, 2H), 8.15 (d, J=8.4 Hz, 2H), 7.81 (d, J=8.4 Hz, 2H), 7.35-7.24 (m, 5H), 7.17-7.09 (m, 4H), 6.42 (d, J=8.0 Hz, 2H), 4.75 (s, 2H), 3.30-3.15 (m, 8H), 2.32 (s, 3H), 2.23 (s, 3H); LC-MS: m/z (ES$^+$) for $C_{18}H_{22}N_2S$ 298 [M+1]$^+$ and m/z (ES$^-$) for $C_{23}H_{16}O_6$ 388 [M−1].

Example 2: Preparation of Vortioxetine Semi Pamoic Acid Salt (r=2)

Method 1: Dissolving pamoic acid (194 mg, 0.5 mmol) and vortioxetine (298 mg, 1 mmol) in 0.7 ml DMSO at room temperature, adding 3 ml distilled water (DMSO:water=1: 4.5), placing it until products of light yellow powder are separated out, and verifying the product using nuclear magnetic resonance hydrogen spectrum and mass spectrum. $^1$H NMR (400 MHz, DMSO) δ:
8.20 (d, J=8.8 Hz, 2H), 8.16 (s, 2H), 7.63 (4, J=8.0 Hz, 2H), 7.34 (d, J=7.6 Hz, 2H), 7.24 (s, 2H), 7.17-7.10 (m, 8H), 7.01-6.92 (m, 4H), 6.42 (d, J=7.2 Hz, 2H), 4.67 (s, 2H), 3.20-3.10 (m, 16H), 2.32 (s, 6H), 2.24 (s, 6H); LC-MS: m/z (ES+) for $C_{18}H_{22}N_2S$ 298 [M+1]+ and m/z (ES−) for $C_{23}H_{16}O_6$ 388 [M−1]−

Figure 1:
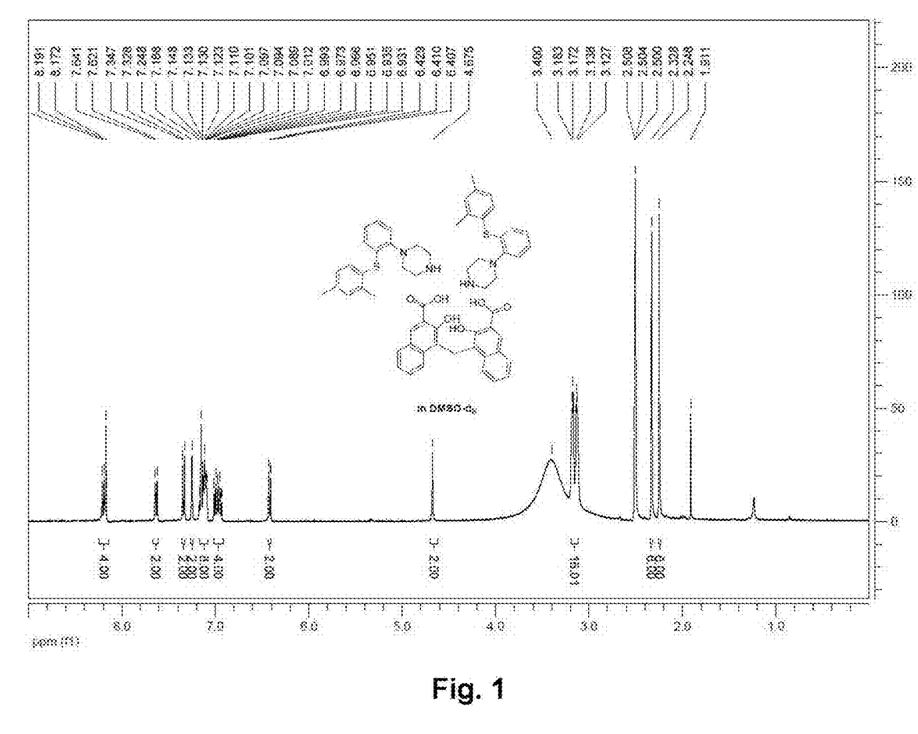
FIG. 1 is a $^1$H-NMR diagram of vortioxetine pamoic acid semi-salt (r=2) in Example 2 of the present application.
Figure 2:
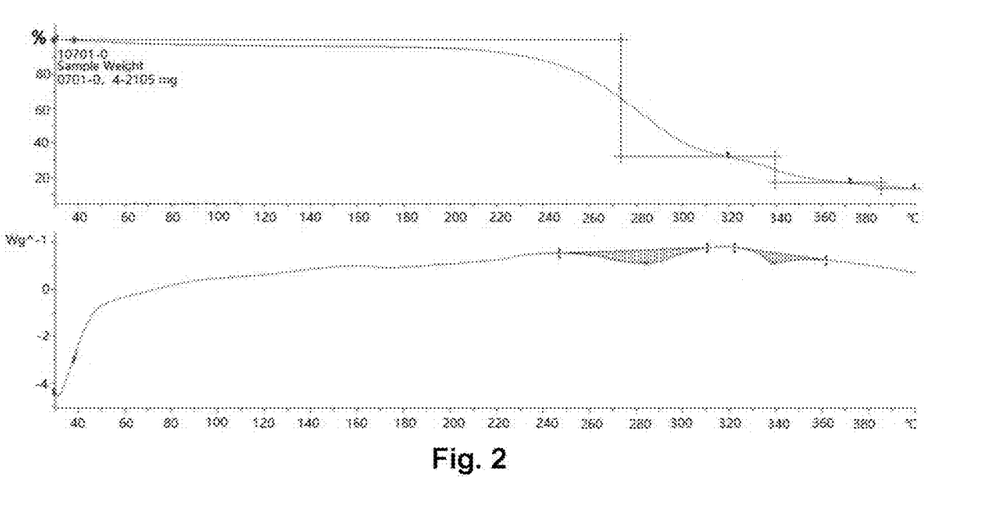
FIG. 2 is a TGA&DSC atlas of vortioxetine pamoic acid semi-salt in Example 2 of the present application.

Method 2: Dissolving vortioxetine (84.3 g, 283 mmol) and glacial acetic acid (17 g, 283 mmol) in 900 milliliter water at room temperature, adding pamoic acid (54.9 g, 141 mmol) and sodium hydroxide (11.3 g, 283 mmol) to the 900 milliliter water respectively, stirring for dissolution, dripping the above prepared vortioxetine acetic acid solution to NaOH aqueous solution of pamoic acid for neutral reaction, stirring for two hours, filtering, washing the filter cake with water for three times, and drying using 50° C. air to obtain 140 g light yellow solid, with a yield rate of 100%, verifying the product by $^1$H-NMR and LC-MS, detecting using powder X ray diffraction (XRD) to demonstrate that the salt is an amorphous salt, and performing thermogravimetric analysis (TG) and differential scanning calorimetry (DSC) detection, referring to FIG. 2 for the results, which shows that the salt has an endothermic peak at 258.71° C., indicating that the solid dissolves and at the same time decomposes, and that the salt has an endothermic peak at 331.13° C., with a weight loss of 68.3977%, indicating that the product decomposes, with a weight loss of 83.6575% at the end of the endothermic peak.

Example 3: Preparation of Crystal Form a Vortioxetine Semi Pamoic Acid Salt

Method 1: Adding vortioxetine pamoic acid semi-salt (1.0 g, 1 mmol) prepared in Example 1 to 150 milliliter methanol, raising the temperature to 55° C., stirring for 1 h, leaving it undisturbed until solids are separated out, filtering, and drying the resulting filter cake to obtain a light yellow solid, and detecting by powder X ray diffraction (XRD) to demonstrate that the solid is a crystal form A.

Method 2: Adding vortioxetine pamoic acid semi-salt (1.0 g, 1 mmol) to 150 milliliter methanol, raising the temperature to 55° C., stirring for 1 h, leaving it undisturbed, and then rapidly or naturally cooling the supernatant to see light yellow solid particles separated out, filtering to obtain solid substances, and detecting the solid substances by X ray diffraction (XRD) to demonstrate that the solid substance is crystal form A.

Method 3: Adding vortioxetine pamoic acid semi-salt (1.0 g, 1 mmol) to 150 milliliter methanol, raising the temperature to 55° C., stirring for h, leaving it undisturbed, and then naturally volatizing the supernatant to see light yellow solids separated out, filtering to obtain solid substances, and detecting the solid substances by X ray diffraction (XRD) to demonstrate that the solid substance is crystal form A.

Method 4: Adding vortioxetine pamoic acid semi-salt (400 mg, 0.4 mmol) to toluene (150 ml), stirring, raising the temperature to 60° C., maintaining at 60° C. for about 1 hr, leaving it undisturbed for 10 min, and then thermally filtering the mother liquid, drying the filter cake to obtain light yellow solids, and detecting by X ray diffraction (XRD) to demonstrate that the solid is crystal form A.

Example 4: Preparation of Crystal Form B Vortioxetine Semi Pamoic Acid Salt

Dissolving vortioxetine pamoic acid semi-salt (133 mg, 0.13 mmol) in 0.5 ml DMSO at room temperature, and then adding 10 ml acetonitrile;

or dissolving vortioxetine pamoic acid semi-salt (133 mg, 0.13 mmol) in 0.5 ml THF at room temperature, and then adding 7.5 ml acetonitrile ethyl acetate, leaving it undisturbed for 15 days;

or dissolving vortioxetine pamoic acid semi-salt (133 mg, 0.13 mmol) in 0.5 ml THF at room temperature, and then adding 1 ml acetone and 1 ml n-heptane, leaving it undisturbed for 4 days;

After swelling crystallization of the above mixed solution, detecting the resulting crystals by X ray diffraction (XRD) to demonstrate that the crystal is crystal form B.

Example 5: Preparation of Crystal Form D Vortioxetine Semi Pamoic Acid Salt

Adding vortioxetine pamoic acid semi-salt (1.0 g, 1 mmol) to 150 ml acetonitrile, stirring for 3 days at room temperature, or adding it to 150 ml acetone, stirring for 5 days at room temperature, and detecting the separated crystals by X ray diffraction (XRD) to demonstrate that the separated crystal is crystal form D.

Example 6: Detection of Crystal Forms Prepared in Example 3, Example 4 and Example 5

Detecting the samples of crystal forms prepared in Example 3, Example 4 and Example 5 in the methods of X ray powder diffraction (XRD), differential scanning calorimetry (DSC), and thermogravimetric analysis (TGA) respectively, wherein the detection conditions of the methods are as follows:

Detection Parameters of Powder X Ray Diffraction (XRD):

Instrument: German Bruker D8-Advance X-ray polycrystalline powder diffractometer, power: 3 KW, scanning range: 2θ: 10°~90°, step width: 0.02°, scanning speed: 5°/min, using Cu target Ka1 ray.

TGA-DSC Detection Parameters:

Thermogravimetric analyzer-differential scanning calorimeter: Mettler Yoledo, TGA/DSC 3+, SNR B608136702, FNR 30139250

Test conditions: heating rate 10° C./min, temperature rising range 25~300° C., balance nitrogen 40 mL/min; flow velocity of sample nitrogen 60 mL/min The test results are shown in Tables 1-3 and FIGS. 3-8.

TABLE 1

Characteristic spectral lines of X-powder diffraction of crystal form A of vortioxetine semi pamoic acid salt

| Diffraction angle 2θ (°) | Peak intensity $I/I_0$ (%) |
| --- | --- |
| 11.71 | 8.2 |
| 12.41 | 8.0 |
| 12.96 | 66.5 |
| 13.56 | 100.0 |
| 14.77 | 46.8 |
| 16.67 | 79.8 |
| 17.26 | 57.5 |
| 18.28 | 96.1 |
| 18.77 | 49.0 |
| 19.98 | 49.1 |
| 21.02 | 35.3 |
| 22.08 | 54.6 |
| 23.03 | 45.5 |
| 24.03 | 28.4 |
| 24.99 | 23.3 |
| 25.94 | 7.3 |
| 27.33 | 22.9 |
| 27.99 | 26.1 |
| 29.797 | 7.3 |
| 30.59 | 18.5 |
| 31.09 | 7.6 |
| 32.70 | 8.8 |
| 35.46 | 7.7 |

TABLE 1-continued

Characteristic spectral lines of X-powder diffraction
of crystal form A of vortioxetine semi pamoic acid salt

| Diffraction angle 2θ (°) | Peak intensity $I/I_0$ (%) |
|---|---|
| 39.21 | 12.3 |
| 42.81 | 8.0 |
| 46.98 | 5.5 |

TABLE 2

Characteristic spectral lines of X-powder diffraction of
crystal form B of vortioxetine semi pamoic acid salt

| Diffraction angle 2θ (°) | Peak intensity $I/I_0$ (%) |
|---|---|
| 11.89 | 1.4 |
| 12.50 | 19.8 |
| 14.93 | 39.4 |
| 15.23 | 55.3 |
| 18.63 | 9.4 |
| 19.37 | 100.0 |
| 20.15 | 10.0 |
| 22.24 | 52.8 |
| 23.25 | 21.9 |
| 24.49 | 24.6 |
| 24.82 | 6.3 |
| 28.28 | 21.9 |
| 30.58 | 10.9 |
| 36.97 | 2.3 |
| 37.58 | 3.0 |
| 38.73 | 6.2 |
| 40.67 | 7.4 |
| 41.81 | 6.1 |

TABLE 3

Characteristic spectral lines of X-powder diffraction of
crystal form D of vortioxetine semi pamoic acid salt

| Diffraction angle 2θ (°) | Peak intensity $I/I_0$ (%) |
|---|---|
| 11.51 | 22.2 |
| 12.34 | 100.0 |
| 16.16 | 35.5 |
| 17.69 | 19.0 |
| 18.05 | 39.4 |
| 18.83 | 5.2 |
| 19.36 | 7.8 |
| 20.08 | 2.3 |
| 21.50 | 19.8 |
| 22.50 | 20.1 |
| 24.01 | 4.3 |

Figure 3:
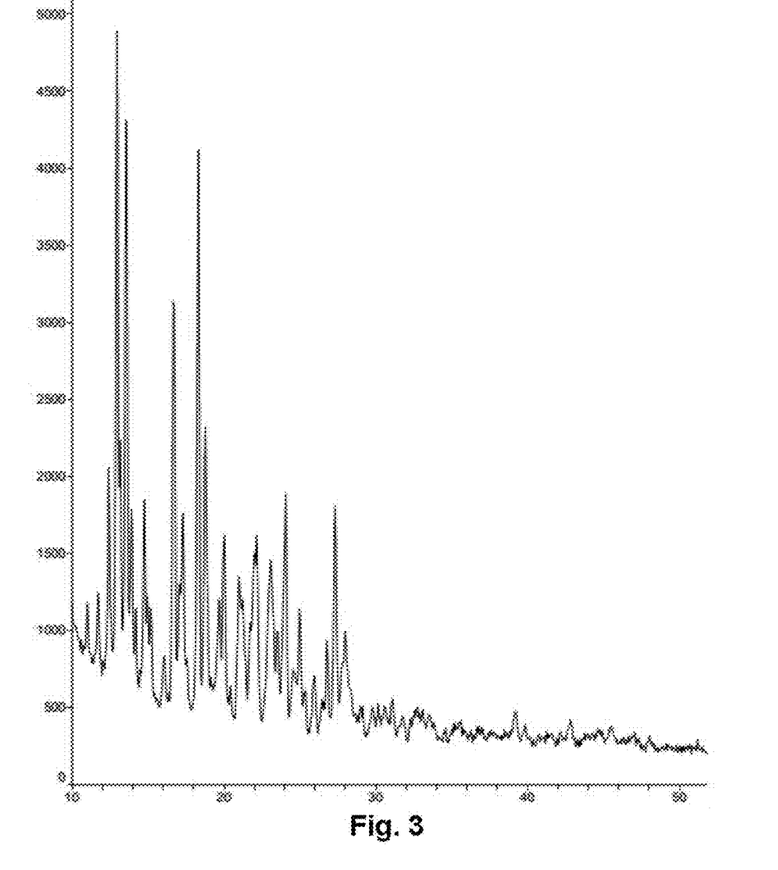
FIG. 3 is an XRD atlas of crystal form A of vortioxetine pamoic acid semi-salt in Example 3 of the present application, wherein the horizontal axis is diffraction angle 2θ(°), and the vertical axis is peak intensity (counts).

As can be seen from FIG. 3 and Table 1, crystal form A has characteristic diffraction peaks at the positions where the angle 2-theta is 12.96, 13.56, 14.77, 16.67, 17.26, 18.28, 18.77, 19.98, 22.08, and 23.03.

Figure 4:
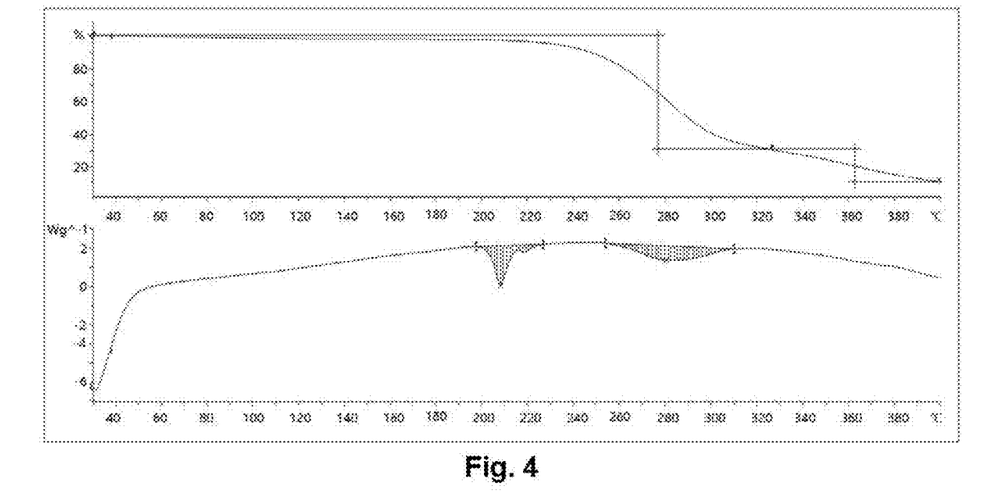
FIG. 4 is a TGA&DSC atlas of crystal form A of vortioxetine pamoic acid semi-salt in Example 3 of the present application.

As can be seen from FIG. 4, crystal A of vortioxetine pamoic acid semi-salt has an endothermic peak at 203.02° C., which is demonstrated to be the crystalline melting point, and has an endothermic peak at 261.73° C., showing obvious weight loss, which demonstrates that the product decomposes, having a weight loss of 69.6217% after the heat absorption is over.

Figure 5:
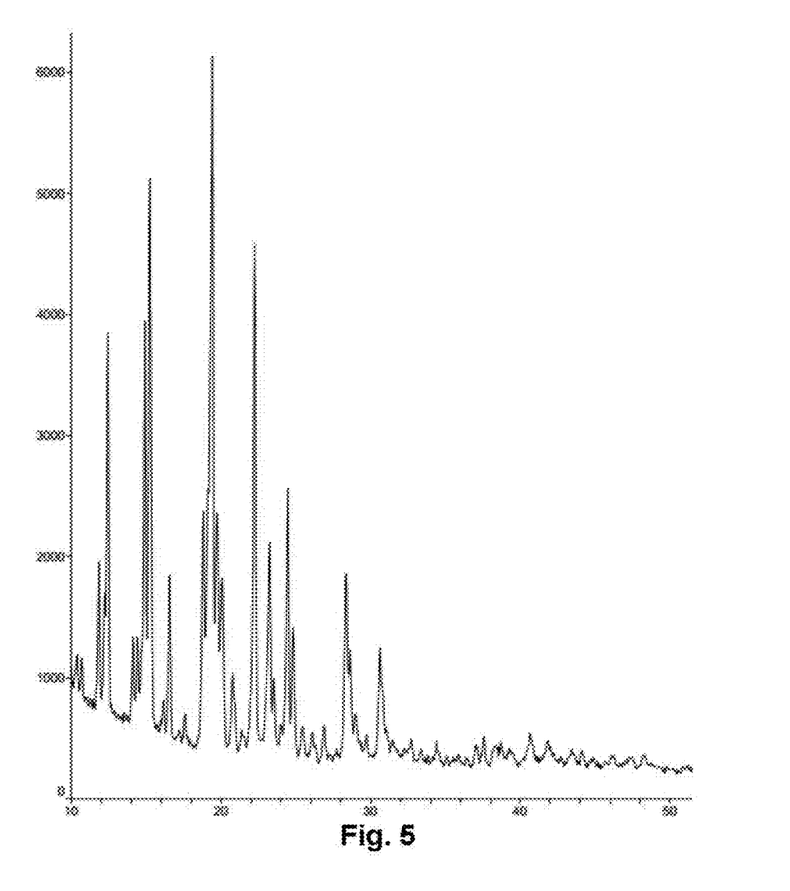
FIG. 5 is an XRD atlas of crystal form B of vortioxetine pamoic acid semi-salt in Example 4 of the present application, wherein the horizontal axis is diffraction angle 2θ(°), and the vertical axis is peak intensity (counts).

FIG. 5 and Table 2 show the atlas of XRD of crystal form B, wherein the crystal form B has characteristic diffraction peaks at the positions where the angle 2-theta is 12.50, 14.93, 15.23, 19.37, 22.24, 23.25, 24.49, 28.28, and 30.58.

Figure 6:
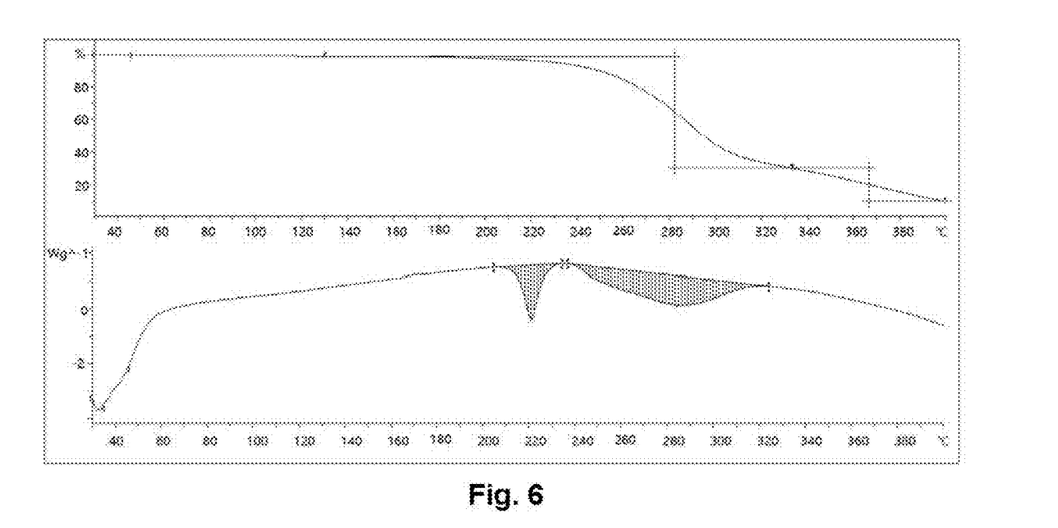
FIG. 6 is a TGA&DSC atlas of crystal form B of vortioxetine pamoic acid semi-salt in Example 4 of the present application.

As can be seen from FIG. 6, crystal B of vortioxetine pamoic acid semi-salt has an endothermic peak at 215.04° C., which is demonstrated to be the crystalline melting point, and has an endothermic peak at 240.10° C., showing obvious weight loss later, which demonstrates that the product decomposes, having a weight loss of 68.7653% after the heat absorption is over.

Figure 7:
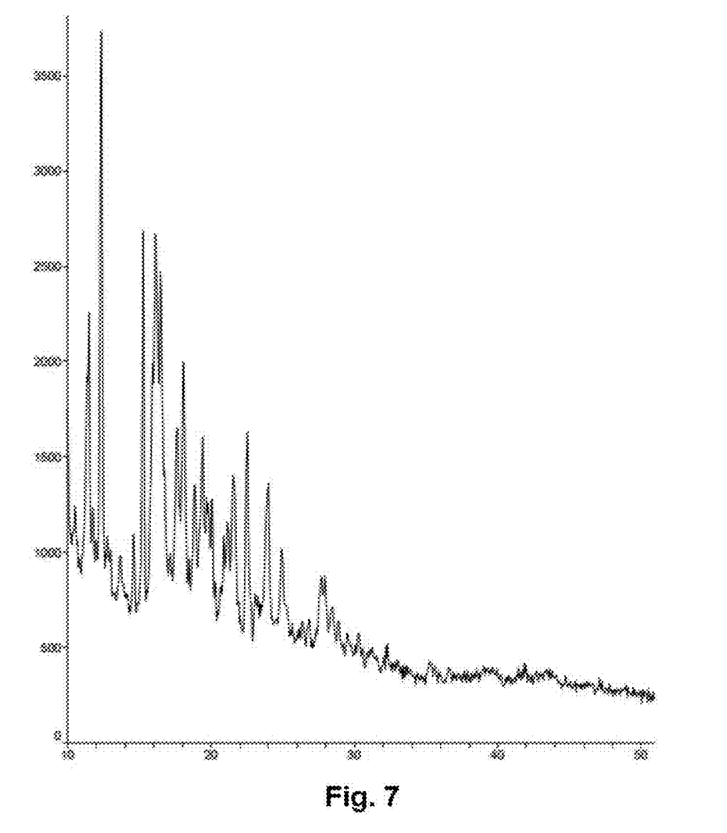
FIG. 7 is an XRD atlas of crystal form D of vortioxetine pamoic acid semi-salt in Example 5 of the present application, wherein the horizontal axis is diffraction angle 2θ(°), and the vertical axis is peak intensity (counts).

As can be seen from FIG. 7 and Table 3, crystal form D has characteristic diffraction peaks at the positions where the angle 2-theta is 11.51, 12.34, 16.16, 16.48, 17.69, 18.05, 19.36, 21.50, 22.50, 24.01, and 27.65.

Figure 8:
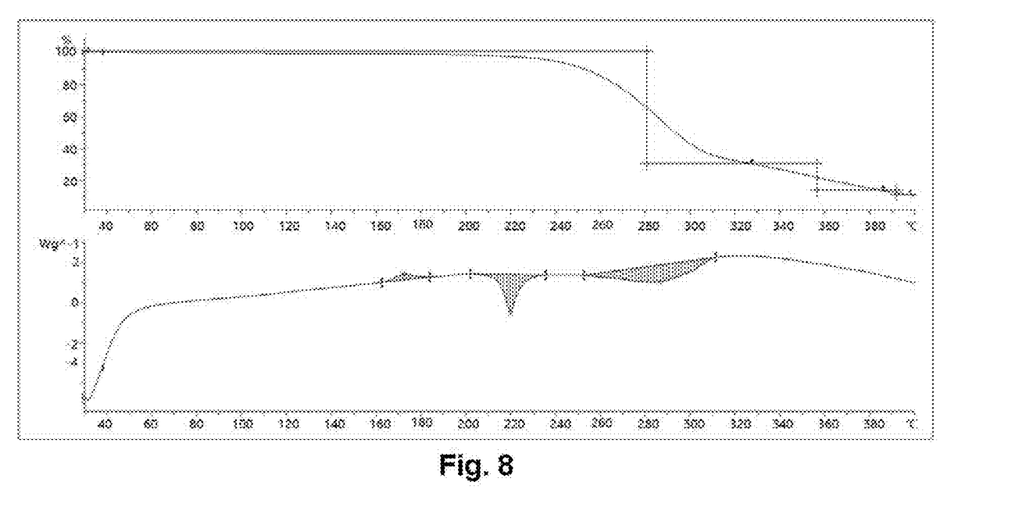
FIG. 8 is a TGA&DSC atlas of crystal form D of vortioxetine pamoic acid semi-salt in Example 5 of the present application.

As can be seen from FIG. 8, crystal D of vortioxetine pamoic acid semi-salt has an endothermic peak at 164.60° C. and 214.65° C. respectively, which are demonstrated to be the crystalline melting points, and has an endothermic peak at 257.38° C., showing obvious weight loss, which demonstrates that the product decomposes, having a weight loss of 69.9723% after the heat absorption is over.

Example 7: Research on Stability of Crystals of Vortioxetine Pamoic Acid Semi-Salt Research on Stability of Crystals of Vortioxetine Pamoic Acid in a Medium Setting crystal form A, crystal form B and crystal form D of vortioxetine semi pamoic acid salt at 65° C. respectively, maintaining for 3 days, then maintaining them at 100° C. for 18 hours, and at 150° C. for 2 hours; detecting by XRD to see whether the crystal forms of the samples are changed; detecting the samples which have been maintained at 150° C. for 2 hours by $^1$H-NMR to see whether impurity has been generated in the crystal forms.

It can be confirmed after comparison that after the above 3 crystals are maintained at 65° C. for 3 days, at 100° C. for 18 hours, and at 150° C. for 2 hours, XRD remains unchanged; after they are maintained at 150° C. for 2 hours, $^1$H-NMR remains substantially unchanged. The above results show that the three crystal forms have good chemical heat stability below 150 degrees Celsius.

Example 8: Pharmacokinetic Study of Crystal Forms of Vortioxetine Semi Pamoic Acid in Bodies of Rats 1. Preparation of Samples Weighing 75.1 mg of each of crystal forms A, B and D of vortioxetine semi pamoic acid, adding 1 mL diluent (water for Injection containing 1% CMC-Na and 5% mannitol) to each of them, and whirling for 2 min to obtain 3 suspensions (pH~7) of 3 crystal forms with a concentration of 45.6 mg/mL.

2. Administering Drugs to Animals

Drugs are administered to 9 male clean Wistar rats (Shanghai Sippr BK Laboratory Animals Ltd) with a weight range of 183.0~186.3 g in accordance with Table 4.

TABLE 4

| Group | Quantity of animals Male | Quantity of animals Female | Test substance | Dose (mg/kg) | Drug administration Concentration of solution(mg/mL)* | Administered volume(mL/kg) | Administration manner | Collected sample |
|---|---|---|---|---|---|---|---|---|
| 1 | 3 | 0 | Crystal form A of vortioxetine semi pamoic acid | 45.6 | 45.6 | 1 | Single intramuscular injection | Blood plasma |
| 2 | 3 | 0 | Crystal form B of vortioxetine semi pamoic acid: | 45.6 | 45.6 | 1 | Single intramuscular injection | Bloods plasma |
| 3 | 3 | 0 | Crystal form D of vortioxetine semi pamoic acid | 45.6 | 45.6 | 1 | Single intramuscular injection | Blood plasma |

3. Sample Collection and Processing

Collecting blood samples by jugular puncture, about 0.2 mL for each sample, resisting against blood coagulation using heparin sodium, placing the collected blood samples on ice, wherein the blood collecting time is as follows: 30 min, 1 hrs, 2 hrs, 4 hrs, 8 hrs, 24 hrs, 48 hrs, 72 hrs, 120 hrs, 168 hrs, 216 hrs, 264 hrs, 312 hrs, 360 hrs, 504 hrs, and 672 hrs before and after administration of drug; placing the collected blood samples on ice, and separating the blood plasma centrifugally (centrifugal condition: 8,000 revolutions/min, 6 minutes, 2-8° C.); storing the collected blood plasma at −70° C. before analysis.

4. Pharmacokinetic Analysis

Separately calculating the pharmacokinetic parameters $AUC_{0-t}$, $AUC_{0-\infty}$, $MRT_{0-\infty}$, $C_{max}$, $T_{max}$, $T_{1/2}$ etc. of the tested samples using a non-compartment model for pharmacokinetic calculation software WinNonlin5.2 according to the blood concentration data of the drug. For samples with a concentration lower than the quantitative lower limit, when the pharmacokinetic parameters are calculated, the samples sampled before reaching $C_{max}$ should be calculated at zero value; after reaching $C_{max}$, the samples at the sample point should be calculated by "below the limit of quantitation" (BLQ).

5. Results and Discussion

Figure 9:
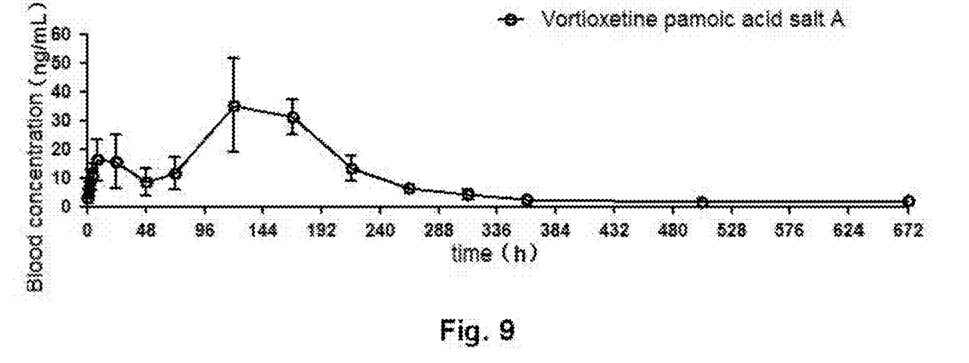
FIG. 9 shows the plasma concentration of vortioxetine in the body of rat after the rat is injected with crystal form A of vortioxetine pamoic acid salt in Example 3 of the present application.
Figure 10:
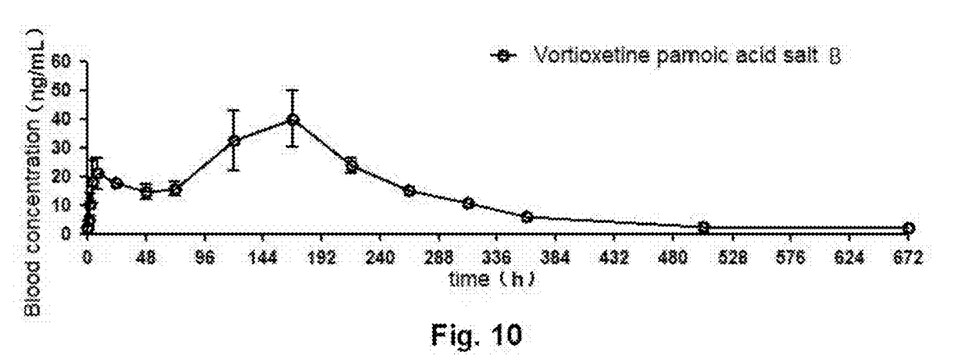
FIG. 10 shows the plasma concentration of vortioxetine in the body of rat after the rat is injected with crystal form B of vortioxetine pamoic acid salt in Example 4 of the present application.
Figure 11:
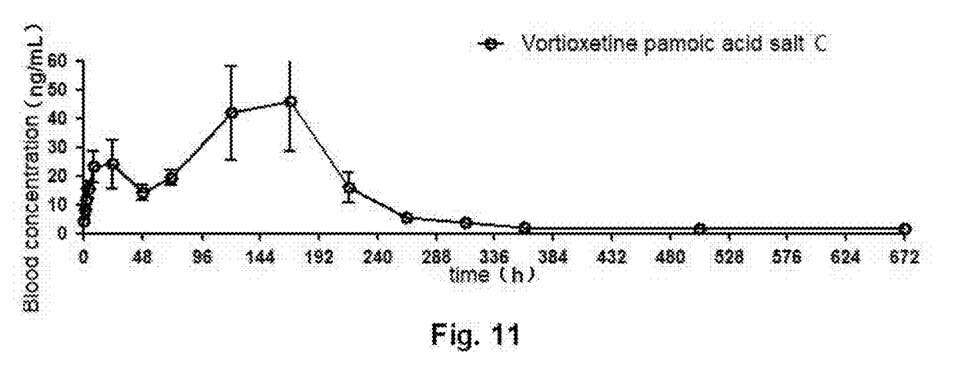
FIG. 11 shows the plasma concentration of vortioxetine in the body of rat after the rat is injected with crystal form D of vortioxetine pamoic acid salt in Example 5 of the present application.

After vortioxetine semi pamoic acid salt is injected to the muscle of the Wistar rat, the test results of plasma concentration in different animals at different time are shown in Table 5, and the corresponding plasma drug concentration-time curve is shown in FIG. 9.

TABLE 5

Concentration of vortioxetine in plasma after injecting the tested sample to muscle of Wistar rat unit: ng/mL

| Blood sampling time (h) | Tested sample Crystal form A of vortioxetine semi pamoic acid salt | | Crystal form B of vortioxetine semi pamoic acid salt | | Crystal form D of vortioxetine semi pamoic acid salt | |
|---|---|---|---|---|---|---|
| | Mean | SD | Mean | SD | Mean | SD |
| 0.5 | 3.12 | 1.77 | 2.14 | 0.60 | 4.34 | 1.67 |
| 1 | 5.80 | 2.93 | 4.56 | 1.56 | 8.10 | 2.10 |
| 2 | 8.41 | 4.66 | 10.17 | 3.98 | 11.59 | 3.81 |
| 4 | 10.75 | 4.59 | 18.05 | 7.34 | 15.37 | 2.70 |

TABLE 5-continued

Concentration of vortioxetine in plasma after injecting the tested sample to muscle of Wistar rat unit: ng/mL

| Blood sampling time (h) | Tested sample Crystal form A of vortioxetine semi pamoic acid salt | | Crystal form B of vortioxetine semi pamoic acid salt | | Crystal form D of vortioxetine semi pamoic acid salt | |
|---|---|---|---|---|---|---|
| | Mean | SD | Mean | SD | Mean | SD |
| 8 | 16.22 | 7.23 | 21.12 | 5.44 | 23.28 | 5.34 |
| 24 | 15.77 | 9.35 | 17.67 | 0.79 | 24.08 | 8.37 |
| 48 | 8.70 | 4.82 | 14.56 | 2.67 | 14.11 | 2.63 |
| 72 | 11.68 | 5.62 | 15.65 | 2.38 | 19.52 | 2.67 |
| 120 | 35.38 | 16.52 | 32.47 | 10.49 | 41.99 | 16.39 |
| 168 | 31.34 | 6.08 | 40.21 | 9.65 | 46.20 | 17.34 |
| 216 | 13.35 | 4.40 | 24.00 | 2.64 | 16.02 | 5.28 |
| 264 | 6.29 | 0.83 | 15.19 | 0.64 | 5.66 | 0.75 |
| 312 | 4.07 | 1.79 | 10.55 | 1.06 | 3.66 | 1.61 |
| 360 | 2.26 | 0.27 | 6.02 | 1.63 | 2.03 | 0.24 |
| 504 | 1.73 | 0.87 | 2.62 | 0.47 | 1.56 | 0.78 |
| 672 | 1.88 | 0.69 | 2.06 | 0.30 | 1.69 | 0.62 |

As can be seen from Table 5 and FIG. 9, after vortioxetine pamoic acid salt is administered for a single time, the concentration of blood in the human body can last for at least 2 weeks, enabling administration once every week or every two weeks, while the vortioxetine hydrobromide clinically used at present shall be administered daily to ensure continuous exertion of the medical effect. Therefore, the vortioxetine pamoic acid salt in the present application can prolong the release of vortioxetine after entering the human body, and can detect the blood concentration of vortioxetine during a long period of time.

The pharmacokinetic parameters of compounds A and B are calculated separately using a non-compartment model for pharmacokinetic calculation software WinNonlin5.2 according to the blood concentration data of the drug,

TABLE 6

Main pharmacokinetic parameters after injecting vortioxetine semi pamoic acid salt to muscle of Wistar rat

| Tested sample | Parameter Unit | $t_{1/2z}$ h | $T_{max}$ h | $C_{max}$ ng/mL | $AUC_{(0-t)}$ ng/mL*h | $AUC_{(0-\infty)}$ ng/mL*h | $MRT_{(0-\infty)}$ h |
|---|---|---|---|---|---|---|---|
| Crystal form A of vortioxetine semi pamoic acid | Mean SD | 126.06 29.58 | 136.00 27.71 | 38.18 11.72 | 6143.08 1886.09 | 6503.21 1747.09 | 227.18 53.61 |
| Crystal form B of vortioxetine semi pamoic acid | Mean SD | 116.6 13.76 | 168 0 | 40.21 9.65 | 8588.42 1016.29 | 8939.49 933.06 | 226.30 29.32 |
| Crystal form D of vortioxetine semi pamoic acid | Mean SD | 228.84 36.96 | 152.00 27.71 | 48.65 17.47 | 7856.57 1919.45 | 8392.02 1893.87 | 162.48 0.93 |

As can be seen from the pharmacokinetic parameters of three crystal forms of vortioxetine pamoic acid salt in Table 6, after a single dose of vortioxetine is injected to the body of the rat, the half-life period $t_{1/2}$ can only reach more than two hours (the data comes from the new drug application documents of vortioxetine submitted by the Takeda Pharmaceutical Company to FDA, i.e., the pharmacological summary document No. 204447Orig 1s000), while the vortioxetine pamoic acid salt prepared in the present application has a half life $t_{1/2}$ of more than 100 hours, greatly delaying the metabolism of vortioxetine in the body.

What is claimed is:

1. A compound, which is a vortioxetine pamoic acid salt, with a structural formula of $(C_{18}H_{22}N_2S)_r \cdot C_{23}H_{16}O_6 \cdot nH_2O$, wherein r is 1 or 2, n=0~10.

2. The compound according to claim 1, characterized in that n is 0, 1, 2, 3, 4, 5 or 6.

3. The compound according to claim 1, characterized in that the vortioxetine pamoic acid salt is a crystalline substance, a solvate, or an amorphous substance.

4. The compound according to claim 3, characterized in that crystal form of the vortioxetine pamoic acid salt is crystal form A, and in an X ray powder diffraction pattern of the crystal form A, there are peaks at positions where 2θ is 12.96±0.2, 13.56±0.2, 16.67±0.2, 17.26±0.2 and 18.28±0.2 degrees.

5. The compound according to claim 4, characterized in that in an X ray powder diffraction pattern of the crystal form A, there are peaks at one or more of positions where 2θ is 14.77±0.2, 18.28±0.2, 18.77±0.2, 19.98±0.2, 22.08±0.2, and 23.03±0.2 degrees.

6. The compound according to claim 4, characterized in that in an X ray powder diffraction pattern of the crystal form A, there are peaks at one or more of positions where 2θ is 11.71±0.2, 12.41±0.2, 14.77±0.2, 18.28±0.2, 18.77±0.2, 19.98±0.2, 21.02±0.2, 22.08±0.2, 23.03±0.2, 24.03±0.2, 24.99±0.2, 25.94±0.2, 27.33±0.2, 27.99±0.2, 29.80±0.2, 30.59±0.2, 31.09±0.2, 32.70±0.2, 35.46±0.2, 39.21±0.2, 42.81±0.2, and 46.98±0.2 degrees, or X ray powder diffraction pattern of the crystal form A is shown in FIG. 3.

7. The compound according to claim 3, characterized in that crystal form of the vortioxetine pamoic acid salt is crystal form B, and in an X ray powder diffraction pattern of the crystal form B, there are peaks at positions where 2θ is 15.23±0.2, 19.37±0.2, and 22.24±0.2 degrees.

8. The compound according to claim 7, characterized in that in an X ray powder diffraction pattern of the crystal form B, there are peaks at one or more of positions where 2θ is 12.50±0.2, 14.93±0.2, 23.25±0.2, 24.49±0.2, 28.28±0.2, and 30.58±0.2 degrees.

9. The compound according to claim 7, characterized in that in an X ray powder diffraction pattern of the crystal form B, there are peaks at one or more of positions where 2θ is 11.89±0.2, 12.50±0.2, 14.93±0.2, 18.63±0.2, 20.15±0.2, 23.25±0.2, 24.49±0.2, 24.82±0.2, 28.28±0.2, 30.58±0.2, 36.97±0.2, 37.58±0.2, 38.73±0.2, 40.67±0.2, and 41.81±0.2 degrees, or X ray powder diffraction pattern of the crystal form B is shown in FIG. 5.

10. The compound according to claim 3, characterized in that crystal form of the vortioxetine pamoic acid salt is crystal form D, and in an X ray powder diffraction pattern of the crystal form D, there are peaks at positions where 2θ is 12.34±0.2, 16.16±0.2 and 18.05±0.2 degrees.

11. The compound according to claim 10, characterized in that in an X ray powder diffraction pattern of the crystal form D, there are peaks at one or more of positions where 2θ is 11.51±0.2, 16.48±0.2, 17.69±0.2, 19.36±0.2, 21.50±0.2, 22.50±0.2, 24.01±0.2, and 27.65±0.2 degrees.

12. The compound according to claim 10, characterized in that in an X ray powder diffraction pattern of the crystal form D, there are peaks at one or more of positions where 2θ is 11.51±0.2, 13.66±0.2, 14.568±0.2, 16.48±0.2, 17.69±0.2, 18.83±0.2, 19.36±0.2, 20.09±0.2, 21.20±0.2, 21.50±0.2, 22.50±0.2, 24.01±0.2, 24.96±0.2, 26.40±0.2, 26.94±0.2, 27.62±0.2, 28.46±0.2, 29.59±0.2, 30.58±0.2, 31.08±0.2, 31.28±0.2, 35.81±0.2, 41.45±0.2, 41.51±0.2, 43.38±0.2, and 48.23±0.2 degrees, or X ray powder diffraction pattern of the crystal form D is shown in FIG. 7.

13. A pharmaceutical composition, comprising a crystal form, a solvate, or an amorphous form of the compound of claim 1 as active ingredients, and pharmaceutically acceptable carriers.

14. The pharmaceutical composition according to claim 13, characterized in that the carrier is a viscous aqueous or non-aqueous carrier.

15. The pharmaceutical composition according to claim 13, characterized in that the carrier comprises a suspending agent, a tension agent and a wetting agent.

16. The pharmaceutical composition according to claim 13, characterized in that the active ingredient exerts a medical effect in a human body for at least 48 hours;

the active ingredient exerts a medical effect in a human body for at least 7 days;

the active ingredient exerts a medical effect in a human body for at least two weeks;

the active ingredient exerts a medical effect in a human body for at least a month.

17. A method for treating depression or pain, comprising administering the pharmaceutical composition according to claim 13 to a patient.

18. The method according to claim 17, wherein the composition is administered by injection.

19. The method according to claim 17, wherein the composition is administered by muscle or subcutaneous injection.

20. The method according to claim 17, characterized in that the drug can be released to the body according to a daily dose of 5-50 mg after administration.

* * * * *